(12) United States Patent
Gibson et al.

(10) Patent No.: US 9,265,859 B2
(45) Date of Patent: Feb. 23, 2016

(54) BIOMEDICAL MATERIALS

(71) Applicants: The University Court of the University of Aberdeen, Aberdeen, Aberdeenshire (GB); ApaTech Limited, Hertfordshire (GB)

(72) Inventors: Iain R. Gibson, Aberdeen (GB); Janet M. S. Skakle, Aberdeen (GB); Daniel J. Hadden, Aberdeen (GB); Thomas Buckland, Hertfordshire (GB)

(73) Assignees: University Court of the University of Aberdeen, Aberdeen, Aberdeenshire (GB); ApaTech Limited, Elstree, Herfordshire (GB)

( * ) Notice: Subject to any disclaimer, the term of this patent is extended or adjusted under 35 U.S.C. 154(b) by 0 days.

(21) Appl. No.: 14/274,014

(22) Filed: May 9, 2014

(65) Prior Publication Data

US 2014/0348943 A1  Nov. 27, 2014

Related U.S. Application Data

(62) Division of application No. 12/595,491, filed as application No. PCT/GB2008/001288 on Apr. 11, 2008, now Pat. No. 8,758,500.

(30) Foreign Application Priority Data

Apr. 11, 2007 (GB) .................................. 0707024.6

(51) Int. Cl.
*C09C 1/02* (2006.01)
*A61L 27/12* (2006.01)
*A61L 27/46* (2006.01)
(Continued)

(52) U.S. Cl.
CPC .............. *A61L 27/12* (2013.01); *A61L 27/025* (2013.01); *A61L 27/46* (2013.01); *C01B 25/322* (2013.01)

(58) Field of Classification Search
CPC . A61K 6/0612; A61K 6/033; A61C 13/0003; A61C 13/0006; A61C 13/0022
USPC ............... 106/35, 691, 462, 463, 464; 264/16
See application file for complete search history.

(56) References Cited

U.S. PATENT DOCUMENTS 6,582,672 B1   6/2003  Bonfield et al.
2008/0262121 A1  10/2008  Landi et al.

FOREIGN PATENT DOCUMENTS

GB          2316940 A      3/1998
GB          2395713 A      6/2004
(Continued)

OTHER PUBLICATIONS

Hijon et al. Dip coated silicon-substituted hydroxyapatite films. Acta Biomaterialia 2 (2006) 567-574.*

(Continued)

*Primary Examiner* — Noah Wiese
(74) *Attorney, Agent, or Firm* — Bret E. Field; Makoto Tsunozaki; Bozicevic, Field & Francis LLP (57) ABSTRACT

The present invention provides a process for the preparation of a silicate and carbonate co-substituted calcium phosphate material. The process comprises the steps of: forming a silicon and optionally carbon-containing calcium phosphate precipitate by an aqueous precipitation method involving preparing an aqueous solution comprising phosphate ions, silicate ions, calcium ions and optionally carbonate ions, wherein the ratio of Ca/P and of Ca/(P+Si) in the solution is maintained above approximately 1.67; and heating the precipitate in an atmosphere comprising carbon and oxygen to form a silicate and carbonate co-substituted calcium phosphate material.
The present invention also provides a synthetic carbonate and silicate co-substituted hydroxyapatite material, as well as a biomedical material.

39 Claims, 4 Drawing Sheets

XRD pattern for EXAMPLE 1

(51) Int. Cl.
*C01B 25/32* (2006.01)
*A61L 27/02* (2006.01)

(56) References Cited

FOREIGN PATENT DOCUMENTS

| WO | WO9808773 A1 | 3/1998 |
|---|---|---|
| WO | WO9932401 A1 | 7/1999 |
| WO | WO2004044274 A1 | 5/2004 |
| WO | WO2007045954 A1 | 4/2007 |

OTHER PUBLICATIONS

Sprio et al. Physico-chemical properties and solubility behaviour of multi-substituted hydroxyapatite powders containing silicon. Materials Science and Engineering C 28 (2008) 179-187.*

Hijon et al., "Dip coated silicon-substituted hydroxyapatite films", Acta Biomater (2006), 2(5):567-574.

Marques et al., "Synthesis and Characterisation of Silicon-Substituted Hydroxyapatite", Proceedings of the 13th Int. Symp. on Ceramics in Medicine; Bologna, Italy (2000), Key Engineering Materials; Bioceramics, p. 247-250.

Sommerauer et al., "A new partial substition mechanism of $CO_3^{2-}$/$CO_3OH^{3-}$ and $SiO_4^{4-}$ for the $PO_4^{3-}$ group in hydroxyapatite from the Kaiserstuhl alkaline compex (SW-Germany)", Contributions to Mineralogy and Petrology (1985), 91(4):360-368.

Sprio et al., "Physico-chemical properties and solubility behaviour of multi-substituted hydroxyapatite powders containing silicon", Materials Science and Engineering: C (2008), 28(1):179-187.

* cited by examiner

Figure 1. XRD pattern for EXAMPLE 1

Figure 2. XRD pattern for EXAMPLE 2

Figure 3. XRD pattern for EXAMPLE 3

Figure 4. XRD pattern for EXAMPLE 4

Figure 5. XRD pattern for EXAMPLE 8

Figure 6. XRD pattern for EXAMPLE 9

Figure 7. Example FTIR pattern

Figure 8. Comparative X-Ray Diffraction Patterns

BIOMEDICAL MATERIALS

The present invention relates to biomedical materials such as synthetic bone replacement materials. In particular, the present invention relates to a carbonate and silicate co-substituted calcium phosphate material and a process for its preparation.

The combined effects of an ageing population and greater expectations in the quality of life have resulted in an increasing global demand for orthopaedic implants for the replacement or augmentation of damaged bones and joints. In bone grafting current gold standards include the use of autograft and allograft but these methods are increasingly recognised as non-ideal due to limitations in supply and consistency. Ceramics have been considered for use as bone graft substitutes to replace or extend traditional bone grafts for over 30 years. In particular, calcium phosphates such as hydroxyapatite have been promoted as a result of their osteoconductive properties.

Accordingly, as surgical technique and medical knowledge continue to advance, there has been a growth in the demand for synthetic bone replacement materials. Consequently, there is an increasing interest in the development of synthetic bone replacement materials for the filling of both load bearing and non-load bearing osseous defects, such as in joint and facial reconstruction.

The biocompatibility of hydroxyapatite, coupled with the similarities between the crystal structure of hydroxyapatite and the mineral content of bone, has led to great interest in hydroxyapatite as a material for the augmentation of osseous defects. The apatite group of minerals is based on calcium phosphate, with stoichiometric hydroxyapatite having a molar ratio of Ca/P of 1.67. Hydroxyapatite has the chemical formula $Ca_{10}(PO_4)_6(OH)_2$. Synthetic hydroxyapatite has been reported as having been used as a bone replacement material in porous, granular, plasma sprayed and dense forms. Investigations have shown hydroxyapatite to be structurally similar to the main inorganic component of human bone. The differences between synthetic and biological hydroxyapatite result in the former being less biologically active and having a lower strength than biological hydroxyapatite. Biological hydroxyapatite has been shown to contain significant amounts of from 3 to 7 wt % of carbonate as well as trace amounts of other elements including sodium, potassium and magnesium. There is evidence that the carbonate group can substitute in two sites, the phosphate (B-Site) and hydroxide (A-Site) sites; biological apatite is predominantly a B type apatite.

Silicon has been shown, in small quantities, to have a significant effect on the development and growth of the hard tissue of living bodies. It has been noted that silicon is localised in active growth areas, such as the osteoid of the young bone of rats and mice. The importance of silicon on bone formation is further supported by the positive properties of bioactive silicate containing glass ceramics and ceramics. It is believed that the silicon enters the hydroxyapatite lattice on the phosphate site (B site). The silicon is thought to exist and/or substitute as a silicon ion or as a silicate ion. PCT/GB97/02325 describes a silicate-substituted hydroxyapatite material.

SUMMARY OF INVENTION

The present invention aims to address at least some of the problems associated with the prior art and to provide novel biomedical materials based on various co-substituted calcium phosphate materials.

Accordingly, the present invention provides a process for the preparation of a silicate and carbonate co-substituted calcium phosphate material, which process comprises:

forming a silicon and optionally carbon-containing calcium phosphate precipitate by an aqueous precipitation method involving preparing an aqueous solution comprising phosphate ions, silicate ions, calcium ions and optionally carbonate ions, wherein the ratio of Ca/P and of Ca/(P+Si) in the solution is maintained at or above approximately 1.67; and heating the precipitate in an atmosphere comprising carbon and oxygen to form a silicate and carbonate co-substituted calcium phosphate material.

DETAILED DESCRIPTION

The present invention will now be further described. In the following passages different aspects/embodiments of the invention are defined in more detail. Each aspect/embodiment so defined may be combined with any other aspect/embodiment or aspects/embodiments unless clearly indicated to the contrary. In particular, any feature indicated as being preferred or advantageous may be combined with any other feature or features indicated as being preferred or advantageous.

The calcium phosphate material will typically comprise an apatite and more preferably hydroxyapatite. The calcium phosphate material is preferably a single phase material or essentially single phase material.

For the avoidance of doubt, the term silicate-substituted as used herein also encompasses silicon-substituted. Likewise, silicon-substituted as used herein also encompasses silicate-substituted. This interpretation applies equally to carbonate-substituted and carbon-substituted.

By the term substituted is meant that the silicate/carbonate ions is substituted into the apatite crystal lattice and is not merely added, in contrast to the prior art.

For the avoidance of doubt, where percentages of silicate/carbonate ions are used herein, these percentages are by weight.

The aqueous solution is advantageously substantially free of non-biocompatible cations. Preferably, the aqueous solution is substantially free of cations other than calcium and hydrogen ions.

The aqueous solution may or may not comprise carbonate ions, although it is preferable that the solution does contain carbonate ions. This facilitates the substitution of more carbonate ions into the structure.

The precipitate will usually be collected and dried prior to the heating step.

The atmosphere in which the precipitate is heated preferably comprises carbon dioxide and also optionally water vapour. The atmosphere preferably comprises from 0 to 0.05 grams of water per liter of gas (eg carbon dioxide), more preferably from 0.005 to 0.05 grams of water per liter of gas. Heating the precipitate in such an atmosphere has been found conducive to obtaining the desired co-substituted material. Small amounts of other gases such as, for example, nitrogen and air may also be present in the atmosphere. In a preferred embodiment the gas comprises only carbon dioxide and optionally water, together with unavoidable impurities.

The pH of the aqueous solution is advantageously maintained alkaline. In particular, the pH of the aqueous solution is preferably greater than 7, more preferably from 9 to 12, still more preferably approximately 10. In order to adjust the pH of the solution to the desired pH, an alkali is preferably added to the solution. The alkali may be, for example, ammonium hydroxide or ammonia.

The heating step will typically comprise calcining and/or sintering of the precipitate, typically at a temperature of from 100° C. to 1500° C., preferably from 600 to 1200° C., more preferably from 900 to 1100° C.

Preferably, during calcining and/or sintering of the precipitate, part or substantially all of the precipitate transforms to an essentially phase-pure synthetic silicate and carbonate co-substituted calcium phosphate material (eg hydroxyapatite) having substantially no impurity phases of, for example, calcium oxide and/or tricalcium phosphate.

The calcining and/or sintering is typically performed for up to 120 hours, preferably from 10 minutes to 4 hours. However, the calcining and/or sintering may be performed for at least 4 hours if further A-type carbonate ion substitution (on the OH site, occurring independently of the other substitutions) is desired.

The process according to the present invention enables materials to be formed which comprise up to approximately 9.37% by weight silicate ions ($SiO_4^{4-}$), which is equivalent to approximately 2.86% by weight silicon, and up to approximately 13% by weight carbonate ions ($CO_3^{2-}$). The material, for example, the calcined/sintered product is preferably essentially phase pure at these levels.

The process according to the present invention preferably results in a material comprising at least 0.1% by weight of silicon. This corresponds to approximately 0.3% silicate ions ($SiO_4^{4-}$). More preferably the material comprises at least 0.3% silicon, more preferably at least 0.5%, still more preferably at least 0.7%. A preferred range of silicon is from 0.1 to 2.8%, more preferably 0.3 to 2% and most preferably from 0.5 to 1.6%.

The process according to the present invention preferably results in a material comprising at least 0.5% by weight carbonate ions ($CO_3^{2-}$), more preferably at least 1% carbonate ions, still more preferably at least 1.5% carbonate ions. A preferred range of carbonate ions is from 1 to 9%, more preferably 2 to 8% and most preferably from 3 to 7%.

The silicate ions are typically substituted in the B site (phosphate site, $PO_4^{3-}$) of the calcium phosphate lattice. The carbonate ions ($CO_3^{2-}$) are also typically substituted in the B site of the calcium phosphate lattice or the B site and the A site (OH, hydroxyl site). The ions are substituted in the lattice and this is in contrast to mere doping of the material.

The amount of carbonate ions substituted in the B site may be controlled by varying the Ca/P molar ratio and/or the relative amount of silicate ions added. For example, for Ca/(P+Si)=1.72, and for 10 moles Ca, 5.62 moles P and 0.19 moles Si, this corresponds to 0.19 moles carbonate on the B-site, or approximately 1.2 wt. % carbonate. Similarly, for Ca/(P+Si)=1.76, and for 10 moles Ca, 5.36 moles P and 0.32 moles Si, this corresponds to 0.32 moles carbonate on the B-site, or approximately 1.9 wt. % carbonate.

The amount of carbonate ions substituted in the A site may be controlled by varying the sintering temperature and sintering time.

The ratio of silicate ions to carbonate ions in the co-substituted calcium phosphate material typically ranges form 1:99 to 99:1, and is preferably approximately 50:50.

The ratio of silicate ions to carbonate ions can be controlled by varying the Ca/P molar ratio and/or the relative amount of silicate ions added. For example, for Ca/(P+Si)=1.76, and for 10 moles Ca, 5.36 moles P and 0.32 moles Si (approximately 2.9 wt. % silicate), this corresponds to 0.32 moles carbonate on the B-site, or approximately 1.9 wt. % carbonate. Similarly, for Ca/(P+Si)=1.76, and for 10 moles Ca, 5.36 moles P and 0.16 moles Si (approximately 1.5 wt. % silicate), this corresponds to 0.48 moles carbonate on the B-site, or approximately 2.9 wt. % carbonate. Similarly, for Ca/(P+Si)=1.76, and for 10 moles Ca, 5.36 moles P and 0.48 moles Si (approximately 4.4 wt. % silicate), this corresponds to 0.16 moles carbonate on the B-site, or approximately 1.0 wt. % carbonate.

The material produced by the process of the present invention may undergo further substitution by various cations. For example, some of the calcium ions may be replaced by, for example, one or more of magnesium, strontium, sodium and yttrium ions. Such substitution may occur independently or dependently on the silicate/carbonate substitution occurring in the phosphate and hydroxyl sites.

The process of the present invention involves aqueous precipitation. The aqueous precipitation preferably comprises:

(i) providing an aqueous solution or solutions comprising a source of phosphate ions, a source of silicate ions and optionally a source of carbonate ions, said solution or solutions preferably being substantially free of cations other than hydrogen ions and optionally calcium ions;

(ii) providing an aqueous solution or suspension comprising a calcium-containing compound; and (iii) mixing the aqueous solution or solutions from (i) with the aqueous solution or suspension from (ii).

The mixing is conducted under conditions such that the reactants react thereby yielding the calcium phosphate precipitate which comprises silicate ions and optionally carbonate ions.

The two or more solutions each comprising one or more of phosphate ions, silicate ions and optionally carbonate ions may be added individually to the aqueous solution or suspension of the calcium-containing compound.

The two or more solutions each comprising one or more of phosphate ions, silicate ions and optionally carbonate ions may be added simultaneously to the aqueous solution or suspension of the calcium-containing compound.

In other words, the solutions can be prepared as individual solutions or as combinations.

The aqueous solution or solutions preferably include(s) a source of carbonate ions comprising carbonic acid and/or a salt thereof. The aqueous solution or solutions comprising carbonic acid and/or salt thereof may be formed by passing a carbon and oxygen-containing gas (eg carbon dioxide) through water.

The source of phosphate ions in the aqueous solution or solutions preferably comprise(s) phosphoric acid and/or a salt thereof. More preferably, the phosphorus-containing compound is selected from one or both of phosphoric acid and/or ammonium phosphate.

The source of silicate ions in the aqueous solution or solutions preferably comprise(s) a silicon or silicate containing compound. Examples include tetraethyl orthosilicate and silicon carboxylates such as silicon acetate.

The calcium-containing compound preferably comprises a calcium salt. Preferably, the calcium salt is selected from one or more of calcium hydroxide, calcium oxide, calcium chloride, calcium nitrate and calcium nitrate hydrate.

A carbon and oxygen-containing gas (eg carbon dioxide) is preferably passed through the solutions of step (i), step (ii) and/or step (iii).

In one embodiment of the process according to the present invention, the carbonate ions in the final product are introduced only during the heating step such that the precipitated product has a molar ratio of Ca/(P+Si) of at least 1.67. In other words, the precipitation is carried out in the absence (or substantial absence) of any added carbonate ions. The heating step may comprise sintering or calcining in a $CO_2$ or $CO_2/H_2O$ atmosphere. Additionally, the source of phosphate ions (hereafter "P") (eg phosphoric acid solution) and the source of silicate ions (hereafter "S") (eg TEOS solution) may be added simultaneously or independently: either P before S; or S before P. Additionally, the source of carbonate ions (hereafter "C") (eg aqueous carbonic acid) may be added to either or both the P and/or S solutions, or it may be added to the solution/suspension of the calcium-containing compound. Furthermore, the S solution may be added to the solution/suspension of the calcium-containing compound prior to the addition of the P solution (with or without the C solution).

In another embodiment, the aqueous solution of step (i) may be prepared by bubbling carbon dioxide through water to form carbonic acid, and then adding P solution (eg $H_3PO_4^-$) and/or S solution(eg TEOS) thereto, or by adding carbon dioxide gas to water under high pressure and then adding P solution and/or S solution. Generally P and S will be added to the solution of carbonic acid in order to provide the $PO_4^{3-}$ and $SiO_4^{4-}$ ions for reaction.

In another embodiment, the aqueous solution of step (i) may be prepared by bubbling carbon dioxide through a solution of P and/or S, or by adding carbon dioxide under pressure to the solutions, in order to form $CO_3^2$ ions in situ. Furthermore, carbon dioxide may be introduced as a solid which carbonates the solution as it vaporises.

The solutions from step (i) are mixed in step (ii) with an aqueous solution or suspension of a calcium-containing compound. This is applicable to all embodiments. For example, a solution of calcium nitrate ($Ca(NO_3)_2$) or a suspension of calcium hydroxide ($Ca(OH)_2$) may be used. Preferably, the mixing will be carried out by drop wise addition of the solutions from step (i) to the calcium-containing solution or suspension. However, bulk mixing of the solution and the suspension may be undertaken provided that the combined mixture is vigorously stirred in order to provide the precipitation reaction.

As an alternative to adding the P+S+C solution (i.e. a "complete" solution) to the calcium-containing solution/suspension, the P and S solutions may be added independently, either simultaneously (from two separate containers) or one after the other. These two solutions may either be both pre-carbonated, or only one of the two solutions may be pre-carbonated, or neither. A further option is to modify any of the above combinations such that the calcium solution/suspension is carbonated although this may, under some conditions, encourage $CaCO_3$ to form.

During the mixing step (ii), carbon dioxide may be bubbled through the mixture.

The ratio of Ca to P in the calcium-containing solution/suspension and the phosphorus-containing solution, when mixed together, is maintained at 1.67 or above.

During and/or after addition of the reactants is complete, the pH of the mixture may be adjusted if need be.

An alkali pH is advantageous to the process and pH 10 to 12 is particularly preferred in order to obtain the desired precipitate. The pH may be adjusted by, for example, the addition of ammonia or another suitable alkali such as ammonium hydroxide. If ammonia or another alkali is added in this manner, then appropriate steps are preferably taken to remove it from the final product.

The precipitate from step (iii) of the process, after collection by, for example, filtering and drying, or by spray-drying, may be calcined/sintered in a wet or dry carbon dioxide atmosphere. In particular, the dried precipitate may be calcined/sintered in carbon dioxide containing up to 0.05 grams of water per liter of gas (preferably 0.01 to 0.05 grams of water per liter of gas) at a temperature in the range of from 100 to 1500° C., preferably from 600° C. to 1200° C. The sintering time will generally be up to 120 hours, preferably 10 minutes to 4 hours. A longer sintering time (>4 hours) may be used if further A-type carbonate ion substitution (on the OH site, occurring independently of the other substitutions by $zCO_3 \leftrightarrow 2zOH^-$) is desired.

The sintering will generally be carried out at atmospheric pressure, i.e. no imposed pressure, although pressures slightly higher than atmospheric may be produced by the particular configuration of the furnace, for example a high pressure furnace.

As noted earlier, carbonate ions need not be introduced during the precipitation stage, but instead by forming a precipitate with a Ca/(P+Si) molar ratio greater than 1.67, and then introducing carbonate substitution on the B-site (and possibly also the A-site) by heating the collected precipitate in a $CO_2$ or a $CO_2/H_2O$ atmosphere. Generally, however, carbonate ions will be introduced in both stages of the process.

In one aspect of the process of the present invention, the carbonate/silicate co-substituted calcium phosphate compositions produced generally comprise up to approximately 2.86% by weight of silicon (equivalent to up to approximately 9.37% by weight $SiO_4^{4-}$) substituted at the B site, and up to approximately 13% by weight of $CO_3^{2-}$ ions substituted in the B site or the B and A sites of the hydroxyapatite structure. Typically the amount of carbonate substitution on the A and B sites will be comparable, but the amount of carbonate substitution on the B-site is controlled mainly by the designed Ca/(P+Si) molar ratio (larger Ca/(P+Si) molar ratios will result in more B-type carbonate substitution), whereas the amount of carbonate substitution on the A-site can be controlled by the sintering time and sintering temperature (longer sintering times will result in more A-type carbonate substitution).

The silicate/carbonate co-substituted hydroxyapatite compositions produced according to the process of the present invention are preferably prepared in the substantial absence of cations other than $Ca^{2+}$ and $H^+$. Accordingly, the compositions do not contain other cations such as $Na^+$ or $NH_4^+$, substituted in their structures, and thus are biocompatible.

The silicate/carbonate co-substituted hydroxyapatite compositions prepared in accordance with the present invention may be used in any of the applications for which hydroxyapatite is used, for example the formation of plasma-sprayed coatings on metallic implants, the formation of porous ceramic bone substitutes, the preparation of composites with polymeric materials such as high density polyethylene, as granules or beads for packing or filling bone defects, as materials for use in chromatography or as materials for use in purification methods such as the removal of heavy metals by adsorption, or as catalysts.

The present invention provided a reliable and economical process for the preparation of a single-phase or an essentially single-phase carbonate and silicate co-substituted calcium phosphate material such as hydroxyapatite. The carbonate and silicate co-substituted calcium phosphate material produced by the process has been found to be thermally stable such that, when a single hydroxyapatite-like phase is required, it will not decompose to undesirable secondary phases such as tricalcium phosphate and calcium oxide upon calcining/sintering. Furthermore, it has been found that the material produced by the process does not lose a significant amount of the carbonate ions that have been substituted into the hydroxyapatite structure during the heat-treatment.

In another aspect, the present invention provides a a synthetic carbonate and silicate co-substituted calcium phosphate material, wherein said material comprises up to approximately 2.86% by weight of silicon (i.e. up to approximately 9.37% by weight silicate) and up to approximately 13% by weight of carbonate ions and is essentially phase-pure with substantially no impurity phases of calcium oxide and/or tricalcium phosphate. The Ca/P ratio is preferably at least 1.67.

The synthetic carbonate and silicate co-substituted calcium phosphate material of the present invention preferably comprises at least 0.1% by weight of silicon.

This corresponds to approximately 0.3% silicate ions ($SiO_4^{4-}$). More preferably the material comprises at least 0.3% silicon, more preferably at least 0.5%, still more preferably at least 0.7%. A preferred range of silicon is from 0.1 to 2.8%, more preferably 0.3 to 2% and most preferably from 0.5 to 1.6%.

The synthetic carbonate and silicate co-substituted calcium phosphate material of the present invention preferably comprises at least 0.5% by weight carbonate ions ($CO_3^{2-}$), more preferably at least 1% carbonate ions, still more preferably at least 1.5% carbonate ions. A preferred range of carbonate ions is from 1 to 9%, more preferably 2 to 8% and most preferably from 3 to 7%.

The calcium phosphate material is preferably hydroxyapatite and the silicate ions are typically substituted in the B site (phosphate), and carbonate ions are typically substituted in the B site or the B site and the A site (hydroxyl site) of the hydroxyapatite structure.

In one embodiment of the present invention, where an essentially phase pure material is required, the phase purity of the material is preferably at least 95%, more preferably at least 97%, still more preferably at least 98%, yet still more preferably at least 99%. In this case the material is substantially free of any secondary phases. It will be appreciated that unavoidable impurities may, however, be present. As will be appreciated, the phase purity of the biomedical material can be measured by conventional X-ray diffraction techniques. In alternative embodiment, higher levels of substitution can be made with the corollary that biocompatible impurities/secondary phases are produced such as calcium carbonate.

The present invention also provides a biomedical material comprising a synthetic carbonate and silicate co-substituted hydroxyapatite material as herein described.

As noted above, the biomedical material may be essentially phase pure or, if desired, it may comprises one or more secondary phases. Examples of secondary phases include one or more of tricalcium phosphate, alpha or beta polymorphs thereof, calcium silicate, tetracalcium phosphate, calcium carbonate, calcium oxide, monetite, brushite, calcium pyrophosphate and octacalcium phosphate. Raising the content of silicate and carbonate above the aforementioned levels tends to produce such secondary phases.

The biomedical material according to the present invention may be used as a synthetic bone material, a bone implant, a bone graft, a bone substitute, a bone scaffold, a filler, a coating or a cement. The biomedical material may be provided in a porous or non-porous form. The biomedical material may be provided in the form of a composite material, for example in conjunction with a biocompatible polymer.

The present invention will be further described with reference to the following non-limiting examples.

The present invention will now be further described further with reference to the following Examples and accompanying drawings in which:—

EXAMPLE 1

$Ca_{10}[(PO_4)_{6-2x}(SiO_4)_x(CO_3)_x][(OH)_2]$ or on heating
$Ca_{10}[(PO_4)_{6-2x}(SiO_4)_x(CO_3)_x][(OH)_{2-2y}(CO_3)_y]$,
where x=0.3

Approximately 20 grams of calcium carbonate powder ($CaCO_3$) (99+% A.C.S.) was heated at 900° C. for more than 16 hours, driving off the carbonate and leaving calcium oxide (CaO).

A suspension of calcium hydroxide was prepared by dispersing 5.6077 g of CaO in 200 mls of deionised water. This suspension was stirred for 15 minutes prior to further reaction to form solution A.

Carbon dioxide ($CO_2$) gas was bubbled into 0.5 liters of deionised water over a period of 30 minutes during which the pH of the solution decreased from approximately 7 to approximately 4. A solution of tetraethyl orthosilicate (TEOS, 98%) was prepared by dissolving 0.6377 g (0.003M) in 200 mls of the $CO_2$-treated water to form solution B.

A phosphoric acid ($H_3PO_4$) solution was prepared by adding 6.2318 g (0.054M) $H_3PO_4$ (85% assay) to 200 mLs of deionised water to form solution C.

Solutions B and C were combined in a separating flask and were added drop-wise and simultaneously to solution A, which was stirred constantly. The addition of solutions B and C took approximately 4 hours and was performed at room temperature. During this addition, the pH of the mixture was maintained between 10.5 and 12.5, if required, using ammonia solution (S.G. 0.88, 35%). After the addition of solutions B and C, the mixture was stirred for a further hour and then aged overnight without stirring. The aged mixture was filtered and the filter cake was washed with two 100 ml portions of deionised water to remove any residual ammonia. The resulting filter cake was dried at 90° C. overnight. The dried filter cake was crushed and ground to a fine powder. The sample was calcined/sintered at 900° C. for 2 hours in $CO_2$ gas, bubbled through water, with the furnace program set to 900° C. at a heating rate of 5° C. $min^{-1}$. On reaching 900° C. the temperature was maintained for 2 hours before cooling to room temperature (10° C. $min^{-1}$).

Figure 1:
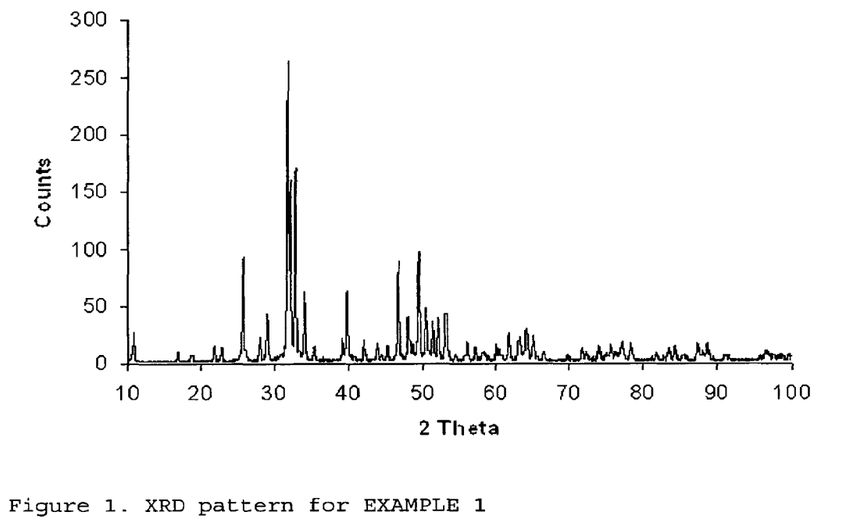
FIGS. 1 to 8 provide XRD patterns for various compositions as described in the Experimental Section, below.

An example of a XRD pattern is shown in FIG. 1.

EXAMPLE 2

$Ca_{10}[(PO_4)_{6-2x}(SiO_4)_x(CO_3)_x][(OH)_2]$ or on heating
$Ca_{10}[(PO_4)_{6-2x}(SiO_4)_x(CO_3)_x][(OH)_{2-2y}(CO_3)_y]$,
where x=0.6

Approximately 20 grams of calcium carbonate powder ($CaCO_3$) (99+% A.C.S.) was heated at 900° C. for more than 16 hours, driving off the carbonate and leaving calcium oxide (CaO).

A suspension of calcium hydroxide was prepared by dispersing 5.6077 g (0.1 moles) of CaO in 200 mls of deionised water. This suspension was stirred for 15 minutes prior to further reaction to form solution A.

Carbon dioxide ($CO_2$) gas was bubbled into 0.5 liters of deionised water over a period of 30 minutes during which the pH of the solution decreased from approximately 7 to approximately 4. A solution of tetraethyl orthosilicate

(TEOS, 98%) was prepared by dissolving 1.2755 g (0.006 moles) in 200 mls of the $CO_2$-treated water to form solution B.

A phosphoric acid ($H_3PO_4$) solution was prepared by adding 5.5338 g (0.048 moles) $H_3PO_4$ (85% assay) to 200 mLs of deionised water to form solution C.

Solutions B and C were combined in a separating flask and were added drop-wise and simultaneously to solution A, which was stirred constantly. The addition of solutions B and C took approximately 4 hours and was performed at room temperature. During this addition, the pH of the mixture was maintained between 10.5 and 12.5, if required, using ammonia solution (S.G. 0.88, 35%). After the addition of solutions B and C, the mixture was stirred for a further hour and then aged overnight without stirring. The aged mixture was filtered and the filter cake was washed with two 100 ml portions of deionised water to remove any residual ammonia. The resulting filter cake was dried at 90° C. overnight. The dried filter cake was crushed and ground to a fine powder. The sample was calcined/sintered at 900° C. for 2 hours in $CO_2$ gas, bubbled through water, with the furnace program set to 900° C. at a heating rate of 5° C. $min^{-1}$. On reaching 900° C. the temperature was maintained for 2 hours before cooling to room temperature (10° C. $min^{-1}$).

Figure 2:
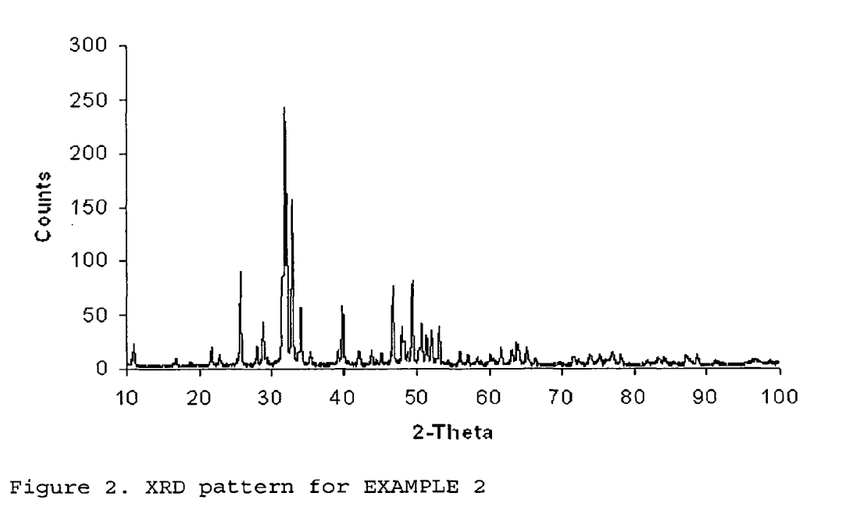

An example of a XRD pattern is shown in FIG. 2.

EXAMPLE 3

$Ca_{10}[(PO_4)_{6-x-z}(SiO_4)_x(CO_3)_z][(OH)_2]$ or on heating
$Ca_{10}[(PO_4)_{6-x-z}(SiO_4)_x(CO_3)_z][(OH)_{2-2y}(CO_3)_y]$,
where x=0.2 and z=0.4

Approximately 20 grams of calcium carbonate powder ($CaCO_3$) (99+% A.C.S.) was heated at 900° C. for more than 16 hours, driving off the carbonate and leaving calcium oxide (CaO).

A suspension of calcium hydroxide was prepared by dispersing 5.6077 g (0.1 moles) of CaO in 200 mls of deionised water. This suspension was stirred for 15 minutes prior to further reaction to form solution A.

Carbon dioxide ($CO_2$) gas was bubbled into 0.5 liters of deionised water over a period of 30 minutes during which the pH of the solution decreased from approximately 7 to approximately 4. A solution of tetraethyl orthosilicate (TEOS, 98%) was prepared by dissolving 0.4252 g (0.002 moles) in 200 mls of the $CO_2$-treated water to form solution B.

A phosphoric acid ($H_3PO_4$) solution was prepared by adding 6.2256 g (0.054 moles) $H_3PO_4$ (85% assay) to 200 mLs of deionised water to form solution C.

Solutions B and C were combined in a separating flask and were added drop-wise and simultaneously to solution A, which was stirred constantly. The addition of solutions B and C took approximately 4 hours and was performed at room temperature. During this addition, the pH of the mixture was maintained between 10.5 and 12.5, if required, using ammonia solution (S.G. 0.88, 35%). After the addition of solutions B and C, the mixture was stirred for a further hour and then aged overnight without stirring. The aged mixture was filtered and the filter cake was washed with two 100 ml portions of deionised water to remove any residual ammonia. The resulting filter cake was dried at 90° C. overnight. The dried filter cake was crushed and ground to a fine powder. The sample was calcined/sintered at 900° C. for 2 hours in $CO_2$ gas, bubbled through water, with the furnace program set to 900° C. at a heating rate of 5° C. $min^{-1}$. On reaching 900° C. the temperature was maintained for 2 hours before cooling to room temperature (10° C. $min^{-1}$).

Figure 3:
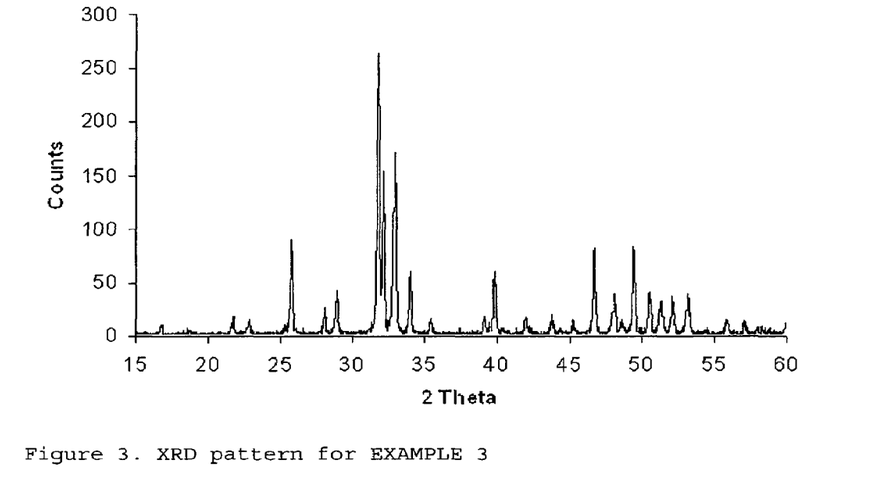

An example of a XRD pattern is shown in FIG. 3.

EXAMPLE 4

$Ca_{10}[(PO_4)_{6-x-z}(SiO_4)_x(CO_3)_z][(OH)_2]$ or on heating
$Ca_{10}[(PO_4)_{6-x-z}(SiO_4)_x(CO_3)_z][(OH)_{2-2y}(CO_3)_y]$,
where x=0.4, z=0.2

Approximately 20 grams of calcium carbonate powder ($CaCO_3$) (99+% A.C.S.) was heated at 900° C. for more than 16 hours, driving off the carbonate and leaving calcium oxide (CaO).

A suspension of calcium hydroxide was prepared by dispersing 5.6077 g (0.1 moles) of CaO in 200 mls of deionised water. This suspension was stirred for 15 minutes prior to further reaction to form solution A.

Carbon dioxide ($CO_2$) gas was bubbled into 0.5 liters of deionised water over a period of 30 minutes during which the pH of the solution decreased from approximately 7 to approximately 4. A solution of tetraethyl orthosilicate (TEOS, 98%) was prepared by dissolving 0.8503 g (0.004 moles) in 200 mls of the $CO_2$-treated water to form solution B.

A phosphoric acid ($H_3PO_4$) solution was prepared by adding 6.2256 g (0.054 moles) $H_3PO_4$ (85% assay) to 200 mLs of deionised water to form solution C.

Solutions B and C were combined in a separating flask and were added drop-wise and simultaneously to solution A, which was stirred constantly. The addition of solutions B and C took approximately 4 hours and was performed at room temperature. During this addition, the pH of the mixture was maintained between 10.5 and 12.5, if required, using ammonia solution (S.G. 0.88, 35%). After the addition of solutions B and C, the mixture was stirred for a further hour and then aged overnight without stirring. The aged mixture was filtered and the filter cake was washed with two 100 ml portions of deionised water to remove any residual ammonia and the resulting filter cake was dried at 90° C. overnight. The dried filter cake was crushed and ground to a fine powder. The sample was calcined/sintered at 900° C. for 2 hours in $CO_2$ gas, bubbled through water, with the furnace program set to 900° C. at a heating rate of 5° C. $min^{-1}$. On reaching 900° C. the temperature was maintained for 2 hours before cooling to room temperature (10° C. $min^{-1}$).

Figure 4:
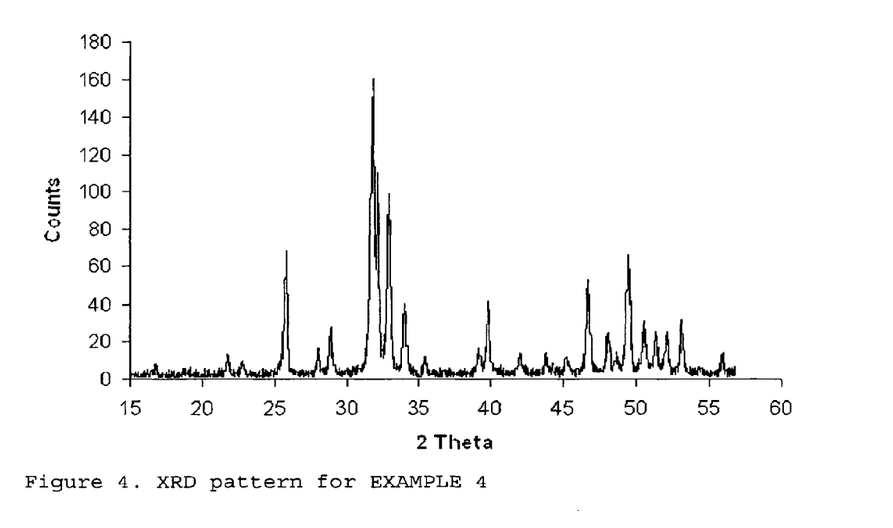

An example of a XRD pattern is shown in FIG. 4.

EXAMPLE 5

In this examples, the order in which solutions B and C were added to solution A was altered in the following procedure. The volumes and concentrations of all reagents were the same as those used in the procedure detailed in Example 1. The differences in the procedure are as follows. Solution C was added drop wise to suspension A and, after complete addition, solution B was added drop wise to the mixture. The pH of the mixture was maintained between 10.5 and 12.5.

The ageing, drying and sintering procedure was the same as detailed in Example 1.

An XRD pattern similar to that shown in FIG. 1 was obtained.

EXAMPLE 6

The order in which solutions B and C were added to solution A was altered in the following procedure. The volumes and concentrations of all reagents were the same as those used in the procedure detailed in Example 1. The differences in the procedure are as follows. Solution B was added drop wise to suspension A and, after complete addition, solution C was added drop wise to the mixture. The pH of the mixture was maintained between 10.5 and 12.5.

The ageing, drying and sintering procedure was the same as detailed in Example 1.

An XRD pattern similar to that shown in FIG. 1 was obtained.

EXAMPLES 7

In this example, the solution(s) prepared using the $CO_2$-treated water were changed. Both solutions B and C were prepared using $CO_2$-treated water and were added to solution A separately or simultaneously as detailed in the above examples. Similarly, the process described above was repeated, but this time the water to make solution C was $CO_2$-treated, then solutions B and C were added to solution A separately or simultaneously as detailed in the above examples.

An XRD pattern similar to that shown in FIG. 1 was obtained.

EXAMPLE 8

To scale-up of the processes described above (e.g. EXAMPLE 1), the only experimental parameter that required changing was the rate of adding solutions B and C to solution/suspension A. Solutions B and C were added either separately or simultaneously to solution/suspension A.

Figure 5:
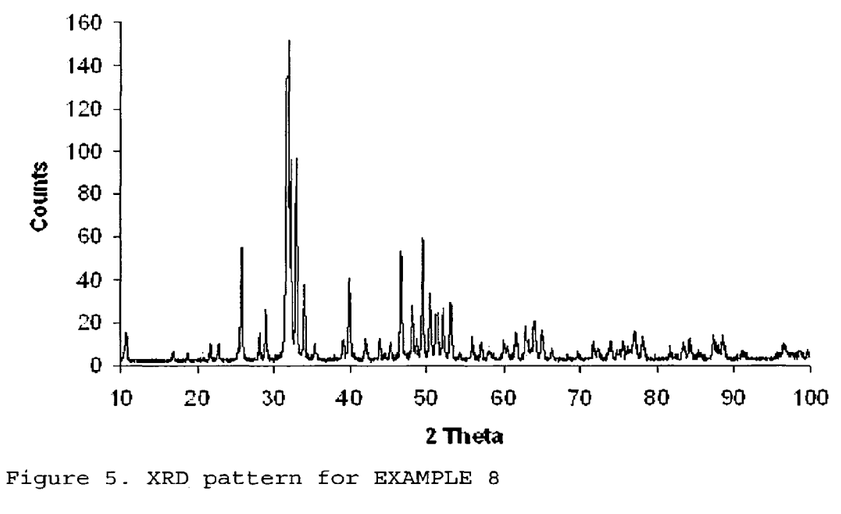

An example of a XRD pattern is shown in FIG. 5.

EXAMPLE 9

$Ca_{10}[(PO_4)_{6-2x}(SiO_4)_x(CO_3)_x][(OH)_2]$ or on heating $Ca_{10}[(PO_4)_{6-2x}(SiO_4)_x(CO_3)_x][(OH)_{2-2y}(CO_3)_y]$, where x=0.3

This sample was prepared as for EXAMPLE 1 but the carbonate ions were only introduced during sintering (in a $CO_2$ or $CO_2/H_2O$ atmosphere) and not during precipitation.

Approximately 20 grams of calcium carbonate powder ($CaCO_3$) (99+% A.C.S.) was heated at 900° C. for more than 16 hours, driving off the carbonate and leaving calcium oxide (CaO).

A suspension of calcium hydroxide was prepared by dispersing 5.6077 g of CaO in 200 mls of deionised water. This suspension was stirred for 15 minutes prior to further reaction to form solution A.

A solution of tetraethyl orthosilicate (TEOS, 98%) was prepared by dissolving 0.6377 g (0.003M) in 200 mls of deionised water to form solution B.

A phosphoric acid ($H_3PO_4$) solution was prepared by adding 6.2256 g (0.054M) $H_3PO_4$ (85% assay) to 200 mLs of deionised water to form solution C.

Solutions B and C were combined in a separating flask and were added drop-wise and simultaneously to solution A, which was stirred constantly. The addition of solutions B and C took approximately 4 hours and was performed at room temperature. During this addition, the pH of the mixture was maintained between 10.5 and 12.5, if required, using ammonia solution (S.G. 0.88, 35%). After the addition of solutions B and C, the mixture was stirred for a further hour and then aged overnight without stirring. The aged mixture was filtered and the filter cake was washed with two 100 ml portions of deionised water to remove any residual ammonia. The resulting filter cake was dried at 90° C. overnight. The dried filter cake was crushed and ground to a fine powder. The sample was calcined/sintered at 900° C. for 2 hours in $CO_2$ gas, bubbled through water, with the furnace program set to 900° C. at a heating rate of 5° C. $min^{-1}$. On reaching 900° C. the temperature was maintained for 2 hours before cooling to room temperature (10° C. $min^{-1}$).

Figure 6:
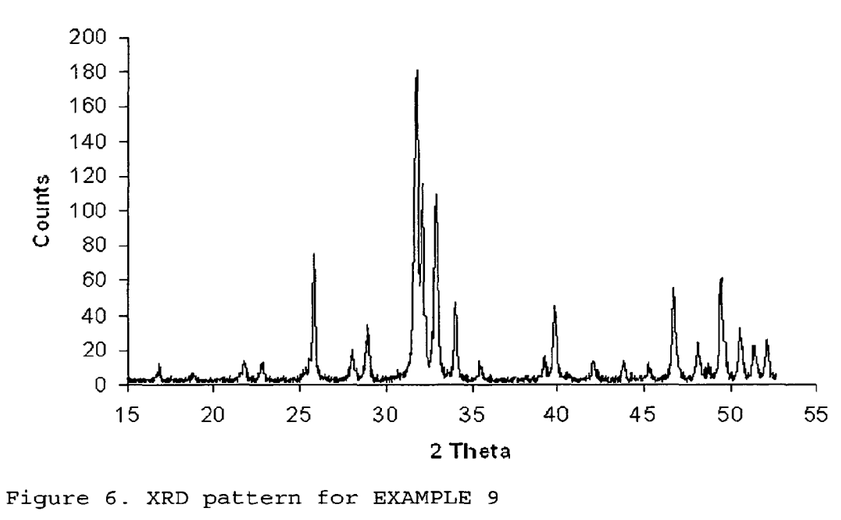

An example of a XRD pattern is shown in FIG. 6.

Analysis of Samples from Examples 1-9

The silicate/carbonate co-substituted hydroxyapatites prepared in Examples 1-9 described above were thermally stable from 700° C. to 1150° C. in a $CO_2/H_2O$ atmosphere. Above these temperatures, partial decomposition to hydroxyapatite and calcium oxide/calcium carbonate/alpha tricalcium phosphate was observed.

The precipitated and calcined/sintered powders were characterized by XRD and FTIR analysis. The X-ray diffraction patterns of calcined/sintered samples show only peaks corresponding to HA. Some patterns show small levels of calcium carbonate (<approximately 2 wt. % of the total) with HA as the main phase (>approximately 98 wt. %). However, lower calcination temperatures (i.e. less than 900° C.) will result in no decomposition to calcium carbonate.

Fourier transform infrared spectroscopy (FTIR) analysis allows the identification of different functional groups, such as OH, $PO_4$, $SiO_4$ and $CO_3$, by their characteristic vibration frequencies; the energy of most molecular vibrations correspond to the infrared region of the electromagnetic spectrum. FTIR spectroscopy is an ideal method for determining the presence or absence of different functional groups in hydroxyapatite. Stoichiometric, non-substituted hydroxyapatite should produce only vibrational bands corresponding to OH and $PO_4$ groups in the FTIR spectrum. In addition to detecting the $SiO_4$ and $CO_3$ groups in a silicate/carbonate co-substituted hydroxyapatite, FTIR spectroscopy should indicate the effect of the $SiO_4$ and $CO_3$ groups on the sites they will be occupying in the hydroxyapatite lattice, i.e. the $PO_4$ and/or the OH groups.

FTIR spectra for the silicate/carbonate co-substituted hydroxyapatite is significantly different from that of non-substituted hydroxyapatite in several ways. First, the appearance of strong bands corresponding to $CO_3$ groups at 1405, 1450, 1540, 880, 873, 870, 755 $cm^{-1}$. Second, the appearance of additional bands in the phosphate $v_1$ and $v_3$ region (1100-900 $cm^{-1}$) plus additional peaks at approximately 950, 650 and 510 $cm^{-1}$, due to the presence of silicate vibrations. Third, a decrease in intensity of the OH stretching vibration at 3570 $cm^{-1}$ and the OH libration peak at 631 $cm^{-1}$ when compared to non-substituted hydroxyapatite.

Figure 7:
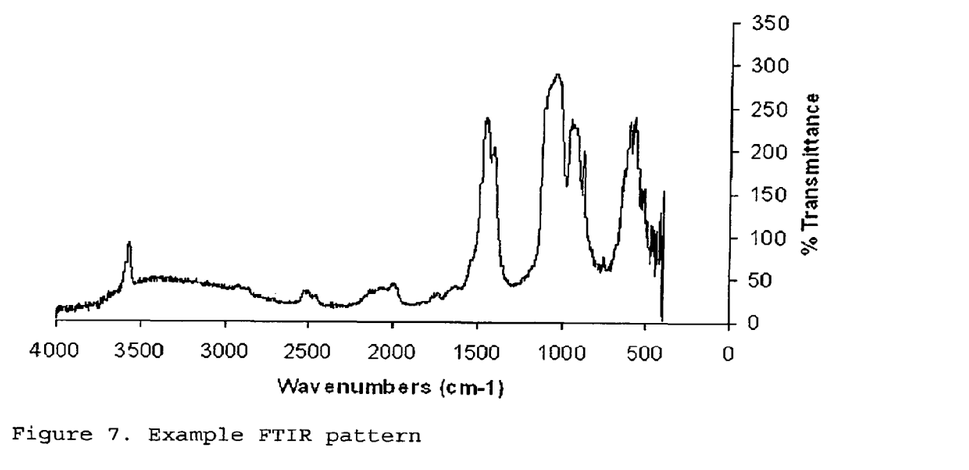

Results of FTIR analysis suggest (see for example FIG. 7—FTIR spectrum of Example 1) that an AB-type silicate/carbonate co-doped hydroxyapatite has been synthesised, as shown by the inclusion of $CO_3$ groups in the spectra along with the OH peak along with evidence supporting $SiO_4$ inclusion.

Decomposition Experiments

The decomposition products of a range of hydroxyapatite compounds were investigated as follows. Samples of hydroxyapatite (no silicate or carbonate), silicate-substituted hydroxyapatite (x=0.3) (no carbonate), silicate/carbonate-substituted hydroxyapatite (x=0.3), and silicate/carbonate-substituted hydroxyapatite (x=0.6) were prepared by aqueous precipitation methods and then sintered in air at 1200° C. for 2 hours.

Figure 8:
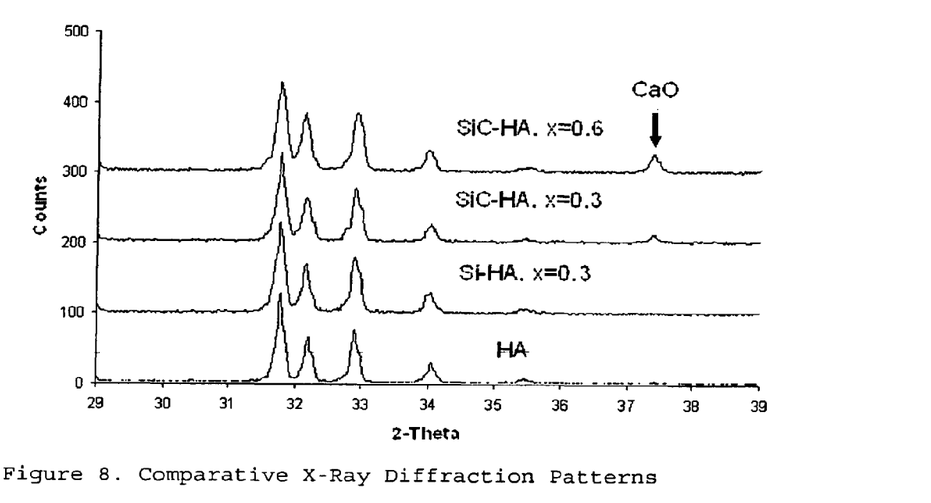

FIG. 8 shows the X-ray diffraction patterns of the samples with the below labels:

hydroxyapatite [HA] (no silicate or carbonate),
silicate-substituted hydroxyapatite [Si-HA, x=0.3] (no carbonate),
silicate/carbonate-substituted hydroxyapatite [SiC-HA, x=0.3], and
silicate/carbonate-substituted hydroxyapatite [SiC-HA, x=0.6].

Both the HA and Si-HA samples produce an X-ray diffraction pattern that contains only hydroxyapatite and no secondary phases. In contrast, the two silicate/carbonate-substituted hydroxyapatite [SiC-HA, x=0.3 and 0.6] produce diffraction patterns that consist of HA and CaO phases (indicated by an arrow), which is indicative of the loss of carbonate from the phosphate site of the hydroxyapatite-like phase, resulting in a Ca-rich composition (Ca/[P+Si]>1.67) which produces CaO as an impurity phase.

The lack of CaO in the diffraction patterns of the HA and Si-HA samples shows that these two phases did not contain any carbonate on the B-site, so that the Ca/[P+Si]=1.67. Any carbonate bands observed in the FTIR spectra of HA or Si-HA sample after precipitation and prior to heating clearly relate to carbonate adsorbed on the surface or labile carbonate, and not carbonate ions within the HA structure on the phosphate site.

In contrast, the presence of CaO on heating in air for silicate/carbonate-substituted hydroxyapatite samples according to the present invention shows that these samples contain carbonate on the phosphate site (as observed by FTIR) and that this is lost on heating in air.

The hydroxyapatite manufactured according to the present invention exhibits properties that more closely match natural biological hydroxyapatites than those presently known in the art. The process of the present invention results in a stronger material than conventional processes and the presence of substituted carbonates in combination with silicates has a significant effect on the development and growth of the hard tissue of living bodies. Furthermore, the bioactivity of the hydroxyapatite is greater.

The invention claimed is:

1. A process for the preparation of a silicate and carbonate co-substituted calcium phosphate material, which process comprises:
   forming a silicon and optionally carbon-containing calcium phosphate precipitate by an aqueous precipitation method involving preparing an aqueous solution comprising phosphate ions, silicate ions, calcium ions and optionally carbonate ions, wherein the ratio of Ca/P and of Ca/(P+Si) in the solution is maintained above approximately 1.67; and
   heating the precipitate in an atmosphere comprising carbon and oxygen to form a silicate and carbonate co-substituted calcium phosphate material.

2. A process as claimed in claim 1, wherein the calcium phosphate material comprises hydroxyapatite.

3. A process as claimed in claim 1, wherein the aqueous solution is substantially free of cations other than calcium and hydrogen ions.

4. A process as claimed in claim 1, wherein the aqueous solution comprises carbonate ions.

5. A process as claimed in claim 1, wherein the precipitate is dried prior to the heating step.

6. A process as claimed in claim 1, wherein the atmosphere comprises carbon dioxide and optionally water.

7. A process as claimed in claim 1, wherein the atmosphere is carbon dioxide and optionally water and unavoidable impurities.

8. A process as claimed in claim 1, wherein the atmosphere comprises from 0 to 0.05 grams of water per liter of gas.

9. A process as claimed in claim 1, wherein the pH of the aqueous solution is maintained alkaline.

10. A process as claimed in claim 9, wherein the pH of the aqueous solution is >7.

11. A process as claimed in claim 1, wherein the heating step comprises calcining and/or sintering of the precipitate at a temperature of from 100° C. to 1500° C., preferably from 600 to 1200° C., more preferably from 900 to 1100° C.

12. A process as claimed in claim 11, wherein during calcining and/or sintering of the precipitate part or substantially all of the precipitate transforms to an essentially phase-pure synthetic silicate and carbonate co-substituted hydroxyapatite material having substantially no impurity phases of calcium oxide and/or tricalcium phosphate.

13. A process as claimed in claim 1, wherein the calcining and/or sintering is performed for up to 120 hours, preferably from 10 minutes to 4 hours.

14. A process as claimed in claim 1, wherein the calcining and/or sintering is performed for at least 4 hours.

15. A process as claimed in claim 1, wherein the calcium phosphate material comprises up to 9.37% by weight silicate ions and up to 13% by weight carbonate ions.

16. A process as claimed in claim 1, wherein the calcium phosphate material comprises at least 0.5% by weight carbonate ions.

17. A process as claimed in claim 1, wherein the calcium phosphate material comprises from 1 to 9% by weight carbonate ions.

18. A process as claimed in claim 1, wherein the silicate ions are substituted in the B site (phosphate site) of the calcium phosphate lattice.

19. A process as claimed in claim 1, wherein the carbonate ions are substituted in the B site of the calcium phosphate lattice or the B site and the A site (hydroxyl site).

20. A process as claimed in claim 19, wherein the amount of carbonate ions substituted in the B site is controlled by-varying the Ca/P molar ratio and/or the relative amount of silicate ions added.

21. A process as claimed in claim 19, wherein the amount of carbonate ions substituted in the A site is controlled by varying the sintering temperature and sintering time.

22. A process as claimed in claim 1, wherein the ratio of silicate ions to carbonate ions in the co-substituted calcium phosphate material ranges from 1:99 to 99:1, preferably approximately 50:50.

23. A process as claimed in claim 1, wherein the ratio of silicate ions to carbonate ions is controlled by varying the Ca/P molar ratio and/or the relative amount of silicate ions added.

24. A process as claimed in claim 1, further comprising cation co-substitution of calcium ions for one or more of magnesium, strontium, sodium and yttrium ions.

25. A process as claimed in claim 1, wherein the aqueous precipitation method involves:
   (i) providing an aqueous solution or solutions comprising a source of phosphate ions, a source of silicate ions and optionally a source of carbonate ions, said solution or solutions preferably being substantially free of cations other than hydrogen ions and optionally calcium ions;
   (ii) providing an aqueous solution or suspension comprising a calcium-containing compound; and
   (iii) mixing the aqueous solution or solutions from (i) with the aqueous solution or suspension from (ii).

26. A process as claimed in claim 25, wherein two or more solutions each comprising one or more of phosphate ions, silicate ions and optionally carbonate ions are added individually to the aqueous solution or suspension of the calcium-containing compound.

27. A process as claimed in claim 25, wherein two or more solutions each comprising one or more of phosphate ions, silicate ions and optionally carbonate ions are added simultaneously to the aqueous solution or suspension of the calcium-containing compound.

28. A process as claimed in claim 25, wherein the aqueous solution or solutions includes a source of carbonate ions comprising carbonic acid and/or a salt thereof.

29. A process as claimed in claim 28, wherein the aqueous solution or solutions comprising carbonic acid and/or salt thereof is/are formed by passing a carbon and oxygen-containing gas through water.

30. A process as claimed in claim 25, wherein the source of phosphate ions in the aqueous solution or solutions comprise (s) phosphoric acid and/or a salt thereof.

31. A process as claimed in claim 25, wherein the source of silicate ions in the aqueous solution or solutions comprise (s) a silicon or silicate containing compound.

32. A process as claimed in claim 31, the source of silicate ions in the aqueous solution or solutions comprise (s) tetraethyl orthosilicate.

33. A process as claimed in claim 31, wherein the source of silicate ions in the aqueous solution or solutions comprise (s) a silicon carboxylate, preferably silicon acetate.

34. A process as claimed in claim 25, wherein the calcium-containing compound comprises a calcium salt.

35. A process as claimed in claim 34, wherein the calcium salt comprises one or more of calcium hydroxide, calcium oxide, calcium chloride, calcium nitrate and calcium nitrate 4-hydrate.

36. A process as claimed in claim 25, wherein a carbon and oxygen-containing gas is passed through the solutions from step (i), step (ii) and/or step (iii).

37. A process as claimed in claim 10, wherein the pH of the aqueous solution is from 9 to 12.

38. A process as claimed in claim 37, wherein the pH of the aqueous solution is approximately 10.

39. A process as claimed in claim 1, wherein the process further comprises, before the heating step:
   drying the silicon and optionally carbon-containing calcium phosphate precipitate; and
   crushing the dried precipitate.

* * * * *